United States Patent
Bock et al.

(10) Patent No.: US 11,004,555 B2
(45) Date of Patent: May 11, 2021

(54) SYSTEM AND METHOD CONSIDERING THE EFFECT OF PHYSICAL ACTIVITY ON THE GLUCOREGULATORY SYSTEM

(71) Applicant: Roche Diabetes Care, Inc., Indianapolis, IN (US)

(72) Inventors: Alain Bock, Chavennes-pres-Renens (CH); David L. Duke, Fishers, IN (US); Abhishek S. Soni, Indianapolis, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 1330 days.

(21) Appl. No.: 13/737,268

(22) Filed: Jan. 9, 2013

(65) Prior Publication Data

US 2013/0130215 A1  May 23, 2013
US 2020/0043370 A9  Feb. 6, 2020

Related U.S. Application Data

(63) Continuation of application No. PCT/EP2011/003622, filed on Jul. 20, 2011.
(Continued)

(51) Int. Cl.
*G01N 33/48* (2006.01)
*G16H 20/17* (2018.01)
(Continued)

(52) U.S. Cl.
CPC ........... *G16H 20/17* (2018.01); *A61B 5/4836* (2013.01); *G09B 19/00* (2013.01); *G09B 23/28* (2013.01);
(Continued)

(58) Field of Classification Search
CPC ................. A61B 5/14523; A61B 5/14532
See application file for complete search history.

(56) References Cited

U.S. PATENT DOCUMENTS 7,979,259 B2 * 7/2011 Brown .................. A61B 5/411
                                                                703/11
2003/0208113 A1 * 11/2003 Mault .................. A61B 5/415
                                                                600/316
(Continued)

FOREIGN PATENT DOCUMENTS

EP         1873667 A2    1/2008

OTHER PUBLICATIONS

Araújo-Vilar, D. et al. Influence of moderate physical exercise on insulin-mediated and non-insulin-mediated glucose uptake in healthy subjects. Metabolism: Clinical and Experimental 46, 203-209 (1997).*
(Continued)

*Primary Examiner* — Soren Harward
(74) *Attorney, Agent, or Firm* — Dinsmore & Shohl, LLP

(57) ABSTRACT

A system and method for considering the effects of aerobic exercise on blood glucose levels for individuals is described. In at least one embodiment of the system of the present disclosure, the system comprises a computing device for generating a prediction of future blood glucose levels for the individual at least partly based on an exercise model, wherein the exercise model is based on parameters that are independent of intensity of the aerobic exercise, and a means for taking an action at least based on the prediction from the exercise model.

20 Claims, 11 Drawing Sheets

Related U.S. Application Data

(60) Provisional application No. 61/367,268, filed on Jul. 23, 2010.

(51) Int. Cl.
*G16H 50/50* (2018.01)
*A61B 5/00* (2006.01)
*A61B 5/145* (2006.01)
*G09B 19/00* (2006.01)
*G09B 23/28* (2006.01)

(52) U.S. Cl.
CPC .......... *G16H 50/50* (2018.01); *A61B 5/14532* (2013.01)

(56) References Cited

U.S. PATENT DOCUMENTS

| | | | | |
|---|---|---|---|---|
| 2005/0192557 A1* | 9/2005 | Brauker | ............... | A61B 5/0002 604/503 |
| 2005/0250995 A1* | 11/2005 | Quy | ............... | A61B 5/0022 600/300 |
| 2006/0189863 A1* | 8/2006 | Peyser | ............... | A61B 5/14532 600/345 |
| 2009/0006061 A1* | 1/2009 | Thukral | ............... | G06F 19/325 703/11 |
| 2009/0006129 A1 | 1/2009 | Thukral et al. | | |
| 2009/0177068 A1* | 7/2009 | Stivoric | ............... | A61B 5/7275 600/365 |
| 2010/0184565 A1* | 7/2010 | Avellino | ............ | A61B 5/02438 482/9 |

OTHER PUBLICATIONS

Bordenave, S. et al. Effects of acute exercise on insulin sensitivity, glucose effectiveness and disposition index in type 2 diabetic patients. Diabetes and Metabolism 34, 250-257 (2008).*

Breton, M. D. Physical activity—the major unaccounted impediment to closed loop control. Journal of Diabetes Science and Technology 2, 169-174 (2008).*

Brun, J. F., Guintrand-Hugret, R., Boegner, C., Bouix, O. & Orsetti, A. Influence of short-term submaximal exercise on parameters of glucose assimilation analyzed with the minimal model. Metabolism 44, 833-840 (1995).*

Roy, A. & Parker, R. S. Dynamic Modeling of Exercise Effects on Plasma Glucose and Insulin Levels. IFAC Proceedings vols. 39, 509-514 (2006).*

Roy, A. & Parker, R. S. Dynamic modeling of exercise effects on plasma glucose and insulin levels. Journal of Diabetes Science and Technology 1, 338-347 (2007).*

A. Roy, R. Parker, "Dynamic Modeling of Exercise Effects on Plasma Glucose and Insulin Levels", Journal of Diabetes Science and Technology, vol. 1, No. 3, May 2007, pp. 338-347.

E. A. Gulve, "Exercise and Glycemic Control in Diabetes: Benefits, Challenges, and Adjustments to Pharmacotherapy", Physical Therapy, vol. 88, No. 11, 2008, pp. 1297-1321.

\* cited by examiner

SYSTEM AND METHOD CONSIDERING THE EFFECT OF PHYSICAL ACTIVITY ON THE GLUCOREGULATORY SYSTEM

CROSS-REFERENCE TO RELATED APPLICATION

The present U.S. utility application a continuation of patent cooperation treaty patent application serial no. PCT/EP2011/003622, filed Jul. 20, 2011, which claims priority to U.S. Provisional Application Ser. No. 61/367,268 filed Jul. 23, 2010, the contents of each of which are hereby incorporated by reference.

BACKGROUND

The present disclosure generally relates to a model of the glucoregulatory system and, in particular, to a model quantifying the effect of physical activity on the glucoregulatory system.

The regulation of blood glucose in diabetics is a perpetual concern. High blood glucose levels, commonly referred to as hyperglycemia, can for example lead to organ damage and/or ketoacidosis, which is a life-threatening condition that needs immediate medical treatment. On the other hand, low blood glucose levels, commonly referred to as hypoglycemia, can lead to unconsciousness or even death. To avoid these conditions, many researchers have tried to understand and develop a model of the glucoregulatory system so that appropriate remedial action can be taken, such as injecting an appropriate insulin dose or ingesting the appropriate foods. The modeling of the glucose regulatory system has been widely studied in the literature over the past 30 years, and continues to be an active research field. One of the key objectives of such models, apart from improving the understanding of the glucoregulatory system, is to allow the prediction of blood glucose concentration, which opens the way for model-based recommendation or control of insulin injection for patients with type 1 diabetes mellitus.

A difficulty that arises is that these models should not only consider the interaction between glucose and insulin, but also include the effects of the carbohydrate intake and physical activity, as they represent two typical factors that change blood glucose concentration. In particular, if the effect of physical activity is neglected, the risk of hypoglycemia during exercise is dramatically increased. While the effect of carbohydrate intake has been widely investigated, only a few exercise models, which rely on the metabolic changes induced by physical activity, have been developed. However, these models are complex and involve a number of model parameters that are too large for proper parameter identification. For example, others have used more complex models to describe the effect of exercise, but are not able to identify the parameters, because the modeled effects are difficult to detect in clinical data.

SUMMARY

According to at least one exemplary embodiment of the present disclosure, a system and method of quantifying the effect of aerobic exercise on blood glucose levels for an individual are provided.

In at least one exemplary embodiment of the method of the present disclosure, the method of quantifying the effect of aerobic exercise on blood glucose levels for an individual, comprises generating with a computing device a prediction of future blood glucose levels for the individual at least partly based on an exercise model, wherein the exercise model is based on parameters that are independent of intensity of the aerobic exercise; and taking an action with the computing device at least based on the prediction from the exercise model.

In at least one embodiment of the method of the present disclosure, the exercise model incorporates an exercise sensitivity value that represents change in the blood glucose level over time during exercise without considering intensity of the exercise. Further, in at least one embodiment, the exercise model accounts for a change in the blood glucose level based on an amplitude of the change in the blood glucose level during exercise for the individual and how quickly the exercise effect appears and disappears in the individual along with an exercise input that considers whether or not an exercise is being performed without considering the intensity of the exercise.

In at least one embodiment of the method of the present disclosure, the exercise model is based on the following equation:

$$\frac{dS_{g,ex}}{dt} = -a_{ex}S_{g,ex} + K_{ex}a_{ex}U_{ex}$$

where $S_{g,ex}$=Exercise glucose effectiveness; $a_{ex}$=Inverse of time constant for exercise effect; $K_{ex}$=Exercise sensitivity; and $U_{ex}$=Exercise input.

In at least one embodiment of the method of the present disclosure, the exercise model is based on the following equation:

$$\frac{dQ}{dt} = -XQ - (S_{g,zero} + S_{g,ex})Q + U_{endo} + U_{g,gut}\frac{g \to mmol}{M}$$

where: Q=glucose amount in the accessible compartment; X=insulin action; $S_{g,zero}$=Glucose effectiveness at hero insulin; $S_{g,ex}$=Exercise glucose effectiveness; $U_{endo}$=Insulin independent endogenous production; $U_{g,gut}$=carbohydrate intake rate; and g→mmol is a constant conversion factor that transforms grams of carbohydrates to mmol.

In at least one embodiment of the method of the present disclosure, the method further comprises receiving an exercise input with the computing device that the aerobic exercise is being or will be performed by the individual. Further, in at least one embodiment, the exercise input is a binary type input that signifies whether or not the aerobic exercise is occurring. Alternately, in at least one embodiment, said receiving the exercise input includes receiving a manual input from the individual. Moreover, in at least one embodiment, said receiving the exercise input includes receiving an automatic input from an exercise monitoring device.

In at least one embodiment of the method of the present disclosure, taking the action with the computing device includes alerting the individual of a dangerous blood glucose level condition. Further, in at least one embodiment of the present disclosure, taking the action with the computing device includes providing an output that educates the individual about the effect of aerobic exercise on blood glucose levels for the individual. Additionally, in at least one embodiment, taking the action with the computing device includes changing an insulin injection profile for an automated pancreas. Moreover, in at least one embodiment, taking the action with the computing device includes performing a bolus calculation.

In at least one embodiment of the method of the present disclosure, the aerobic exercise occurs in a range of aerobic exercise of a maximum heart rate for the individual.

In at least one embodiment of the method of the present disclosure, the method further comprises conducting an exercise study to determine the parameters for the exercise model. Further, in at least one embodiment, only blood glucose concentrations during the exercise study are used to determine the parameters for the exercise model. In at least one embodiment, the exercise study is performed in an office of a physician or at home.

In at least one embodiment of the method of the present disclosure, the exercise has a duration of no more than 90 minutes, no more than 45 minutes, or no more than 30 minutes.

In at least one embodiment of the method of the present disclosure, the computing device includes a glucose meter.

According to at least one embodiment of the method of the present disclosure, the method comprises generating with a computing device a prediction of future blood glucose levels for the individual at least based on an exercise model, wherein the exercise model is based on parameters wherein the only non-constant and measured parameter is an Exercise Input indicating whether an exercise is performed or not; and taking an action with the computing device at least based on the prediction from the exercise model. In at least one embodiment, the only measured variable of the model is a glucose value.

According to at least one embodiment of the present disclosure, a system is provided that is operable to perform the method according to any preceding embodiment.

According to at least one embodiment of the system for quantifying the effect of exercise on blood glucose levels according to the present disclosure, the system comprises a computing device for generating a prediction of future blood glucose levels for the individual at least partially based on an exercise model, wherein the exercise model is based on parameters that are independent of intensity of the aerobic exercise. The system further comprises a means for taking an action at least based on the prediction from the exercise model.

In at least one embodiment of the system of the present disclosure, the means for taking the action includes an automated pancreas.

BRIEF DESCRIPTION OF THE DRAWINGS

The features and advantages of the present disclosure, and the manner of attaining them, will be more apparent and better understood by reference to the following descriptions taken in conjunction with the accompanying figures, wherein.

DETAILED DESCRIPTION

Figure 1:
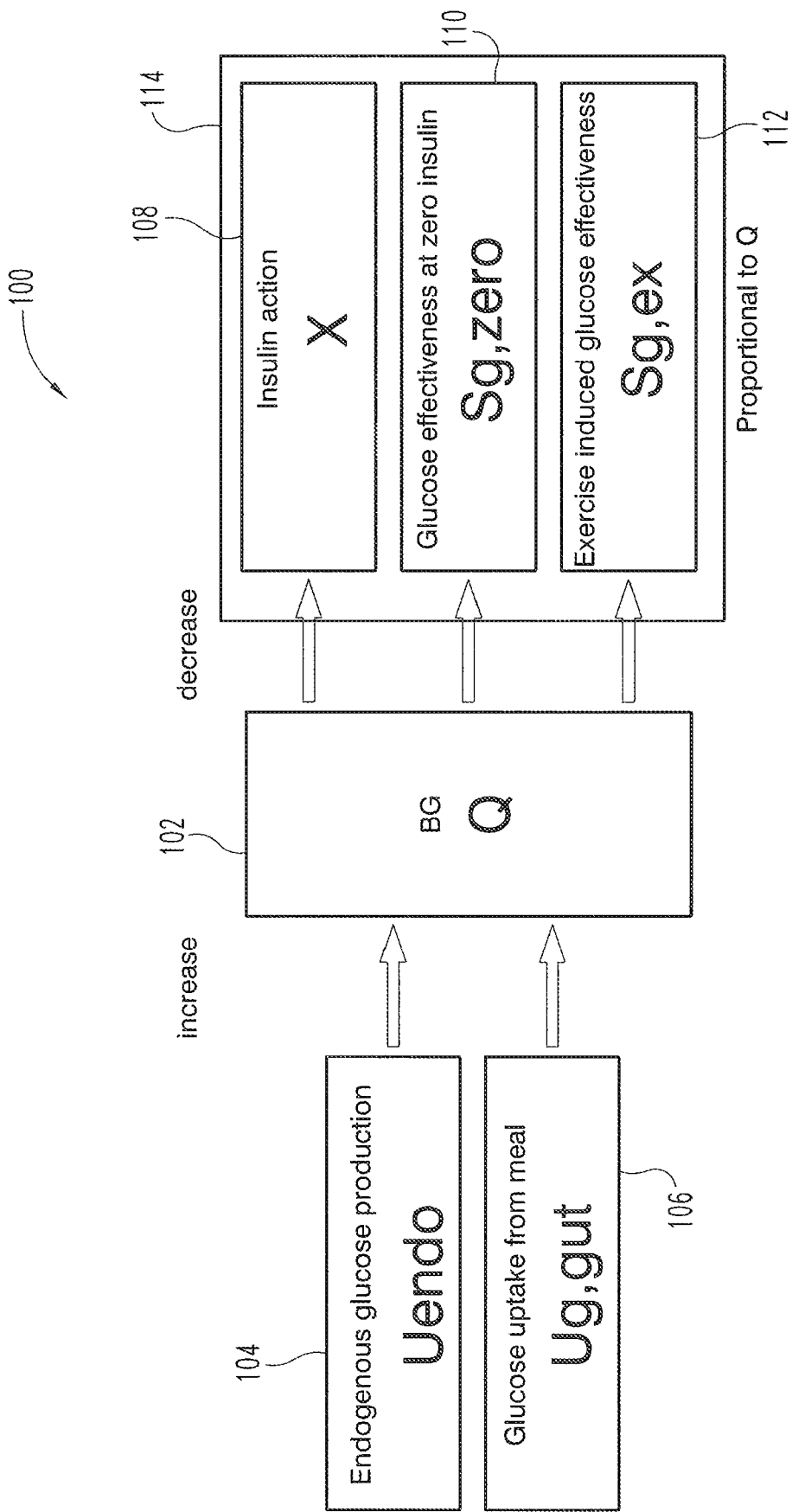
FIG. 1 shows a block diagram of the parameters used in one exemplary embodiment of a model of the present disclosure on how exercise affects blood glucose levels.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended. For instance, logical, mechanical, and electrical changes may be made without departing from the spirit and scope of the present disclosure.

The technique and model described herein address the issues mentioned above, as well as other issues, by facilitating a better understanding of the effect of physical activity on blood glucose concentrations in type 1 diabetics as well as in others.

As discussed above, many models have been developed to consider the interaction between glucose and insulin along with the effects of the carbohydrate intake. However, very few models consider the effect of exercise. For example, in the Adaptive Bolus Pattern (ABP) context, an identifiable model based on the Bergman minimal model has been developed. It is designed to consider meals, but it does not consider exercise. Since every meal is different, each meal is considered as separate input. The model equations for only one meal input are the following:

$$\frac{dU_{g,gut}}{dt} \dot{U}_{g,gut} \qquad \text{Equation 1}$$

$$\frac{d\dot{U}_{g,gut}}{dt} = -2aU_{g,gut} - a^2 U_{g,gut} + K_g a^2 U_{CHO} \qquad \text{Equation 2}$$

$$\frac{dQ}{dt} = -XQ - S_{g,zero}Q + U_{endo} + U_{g,gut} \frac{g \to mmol}{M} \qquad \text{Equation 3}$$

$$\frac{dX}{dt} = -a_x X + a_x X_1 \qquad \text{Equation 4}$$

$$\frac{dX_1}{dt} = -a_x X_1 + K_x a_x \frac{U_{i,sq}}{M} \qquad \text{Equation 5}$$

where:

Q=glucose amount in the accessible compartment [mmol/kg]

X=insulin action [min$^{-1}$]
X$_1$=first compartment insulin action [min$^{-1}$]
U$_{g,gut}$=carbohydrate intake rate [g/min]
U̇$_{g,gut}$=carbohydrate intake rate time derivative [g/min/min]
U$_{CHO}$=rate of ingested carbohydrates in [g/min]
U$_{i,\,sq}$=insulin infusion rate in [mU/min]
and the parameters are the following:
M=Body weight [kg]
V$_{ga}$=Volume of the accessible compartment per body mass [l/kg]
K$_g$ Bioavailability for fast meals [-]
a$_g$=Inverse of time constant for meal absorption [min$^{-1}$]
K$_x$—Insulin sensitivity [kg/mU]
S$_{g,zero}$=Glucose effectiveness at zero insulin [min$^{-1}$]
a$_x$=Inverse of the time constant of the insulin absorption/action [min$^{-1}$]
U$_{endo}$=Insulin independent endogenous production [mmol/kg/min]
g→mmol is a constant conversion factor that transforms grams of carbohydrates to mmol. Its value is 5.551 [mmol/g].

This particular model can reproduce the behavior of the glucose/insulin system with the necessary precision for the ABP application when it is perturbed by a meal. However, changes due to exercise are not modeled in this example. Other previous models, which considered the effect of exercise, were based on the somewhat intuitive assumption that any change in blood glucose concentration depended on the intensity of the exercise, but this approach required a complex set of parameters that were difficult to collect in any practical sense.

The inventors have developed a model that uses a minimalistic approach in determining the effect of exercise on blood glucose levels. That is, the parameters for determining the effect of exercise on blood glucose levels has been reduced to two parameters based on the unexpected discovery that the changes over time in the blood glucose concentration do not generally vary depending on the intensity of the physical activity or exercise, at least within certain ranges.

FIG. 1 schematically represents the relationship of the parameters used in this model. FIG. 1 generally shows a block diagram 100 of the various parameters that affect blood glucose levels. Most of these parameters have already been mentioned with respect to the ABP model described above, especially with respect to Equation 3. As shown, blood glucose amounts 102 (Q) are increased via endogenous glucose production 104 (U$_{endo}$) and glucose uptake through meals 106 (Ug,gut). The blood glucose amount 102 (Q) is related to the blood glucose concentration G via the formula:

G in [mmol/l]=Q/V$_{GA}$, where V$_{GA}$ is the accessible volume per body mass in [l/kg].

As should be appreciated, endogenous glucose production 104 (U$_{endo}$) can occur when the liver and/or muscles break down stored glycogen (glycogenolysis) and release glucose into the bloodstream. Glucose uptake through meals 106 (Ug,gut) occurs when an individual's body creates glucose as a result from ingesting food (or drink). According to Equation 3 of the previously mentioned ABP model, blood glucose amount 102 (Q) can drop because of two reasons. First, there is an insulin action 108 (X) induced drop, and second, there is a drop dependent on the glucose effectiveness at zero insulin 110 (S$_{g,zero}$). It should be recognized that insulin stores nutrients right after a meal by reducing, among other things, the concentrations of glucose in the bloodstream. For instance, insulin stimulates the liver and muscle cells to store glucose in the form of glycogen. This increased uptake of glucose from the bloodstream created by the insulin action 108 (X) reduces the blood glucose amount 102 (Q). The glucose effectiveness at zero insulin 110 (S$_{g,zero}$) parameter represents the insulin independent uptake of glucose from the bloodstream (i.e., no insulin causes the uptake of glucose).

It has been previously found that the drop in blood glucose amount 102 (Q) in diabetic patients is due to increased glucose uptake, while endogenous glucose production 104 (U$_{endo}$) stays the same. This in turn generally means that glucose effectiveness at zero insulin 110 (S$_{g,zero}$) increases during exercise but the endogenous glucose production 104 (U$_{endo}$) stays constant. Based on this understanding, the inventors developed an exercise model that introduces a new parameter, termed exercise glucose effectiveness 112 (S$_{g,ex}$). As shown in FIG. 1, exercise glucose effectiveness 112 (S$_{g,ex}$) is another source for reducing the blood glucose amount 102 (Q). Like insulin action 108 (X) and glucose effectiveness at zero insulin 110 (S$_{g,zero}$) parameters in Equation 3, the exercise glucose effectiveness 112 (S$_{g,ex}$) parameter is proportional to blood glucose amount 102 (Q), as is indicated by box 114 in FIG. 1. In this exercise model, Equation 3 is modified to incorporate the exercise glucose effectiveness 112 (S$_{g,ex}$) parameter. In Equation 6 below, exercise glucose effectiveness 112 (S$_{g,ex}$) parameter has been introduced into Equation 3 in the following manner:

$$\frac{dQ}{dt} = -XQ - (S_{g,zero} + S_{g,ex})Q + U_{endo} + U_{g,gut}\frac{g \to mmol}{M} \qquad \text{Equation 6}$$

where:
S$_{g,ex}$=Exercise glucose effectiveness [min$^{-1}$]

In developing the model, clinical studies were performed to locate variables that caused a change in the exercise glucose effectiveness 112 (S$_{g,ex}$) factor. In one example, a clinical study was performed on 12 patients. They were admitted to the hospital on the first day and measurements were started. On the second day an ergometer workout was performed at 16 h00 (i.e., 4:00 p.m.) at an intensity of 65% of the maximum heart rate for 30 minutes. Insulin management was performed as usual by the patients. On the third day another workout was scheduled at the same time (i.e., 4:00 p.m.) and with the same duration (i.e., 30 minutes), but the exercise was performed with an intensity of 75% of the maximum heart rate. In this instance, insulin management was again adapted by the patient, and meals were not standardized but were in most cases recorded as well.

Exercise can be roughly divided into two physiological, modes: aerobic exercise, often referred to as moderate intensity exercise; and anaerobic exercise, often referred to as high intensity exercise. These define two regions of intensity of the exercise. For Example, the region of intensity on which aerobic exercise occurs can be defined as in the range of 50%-85% of maximal aerobic capacity (VO$_2$ max) or as in the range of 50%-85% of Heart Rate Reserve or as 60% to 90% of maximal Heart Rate. The Maximum Heart Rate can be calculated by the rule of thumb as:

Maximum Heart Rate=220-age.

The Heart Rate Reserve can be calculated as:

Heart Rate Reserve=Maximum Heart Rate-Resting Heart Rate, wherein the Resting Heart Rate is the Heart Rate at resting i.e. without performing any exercise.

With the clinical study described above, the exercise intensities were between 65% and 75%, which falls in the aerobic category. As will be explained below, it has been deduced from the clinical studies that exercise intensity does not play a relevant role in this range. On the other hand, if anaerobic exercise is performed, the human body's reaction is completely different compared to aerobic exercise. In the case of anaerobic exercise, blood glucose concentrations tend to increase, contrary to the moderate or aerobic exercise in which blood glucose levels tend to become lower. For the clinical studies in developing this exercise model, the exercise durations were about 30 and 45 minutes. After exercising for about 90 minutes, the physiological process changes because the hepatic glycogen stocks are depleted. However, it is rather unusual for an average person to exercise for more than 90 minutes. Consequently, the exercise model below will generally focus aerobic exercise or activities having a duration of no more than 90 minutes.

Figure 2:
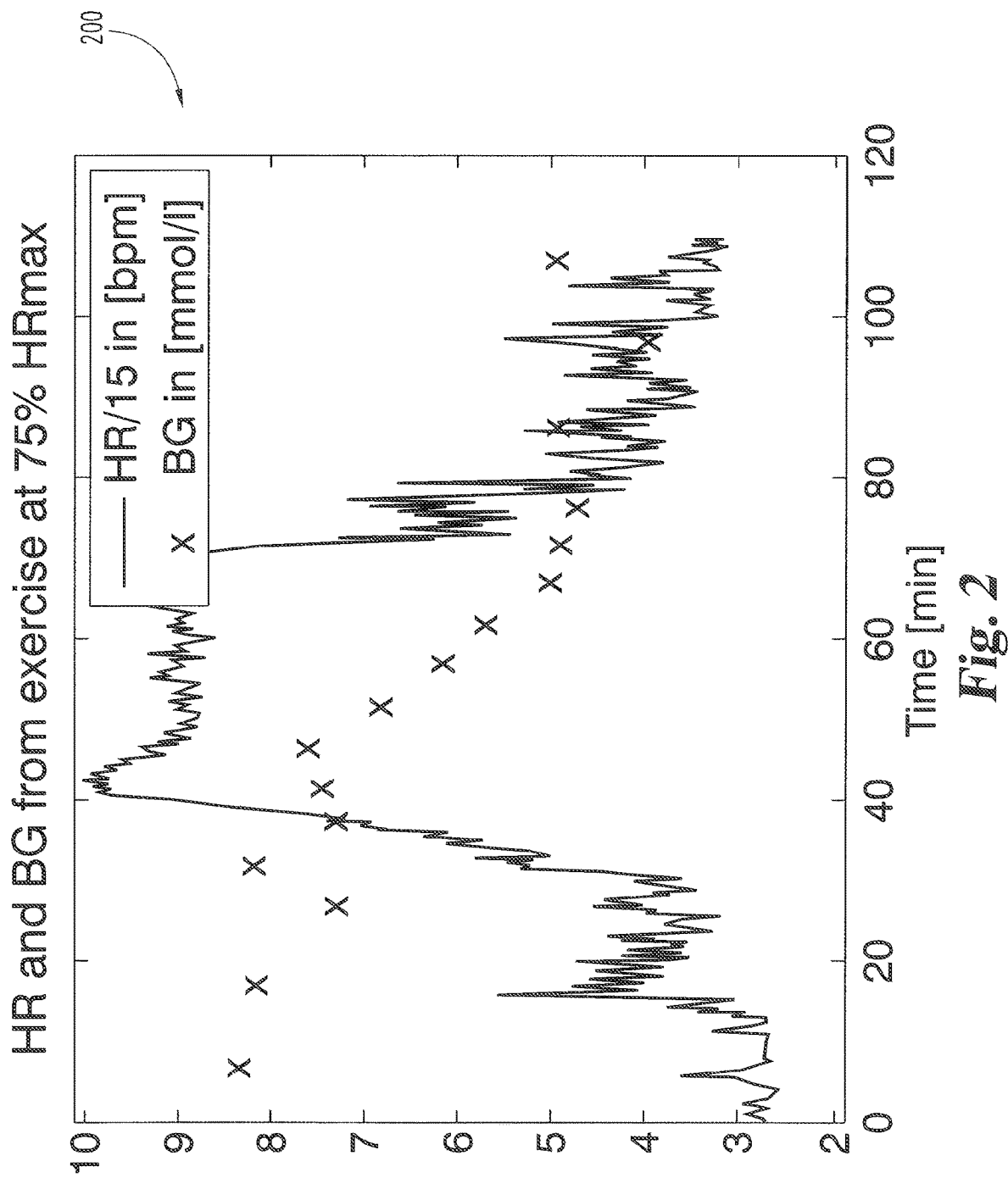
FIG. 2 shows a graph 200 that shows heart rate and blood glucose concentration during exercise at approximately 75% of the maximum heart rate for an individual patient.
Figure 3:
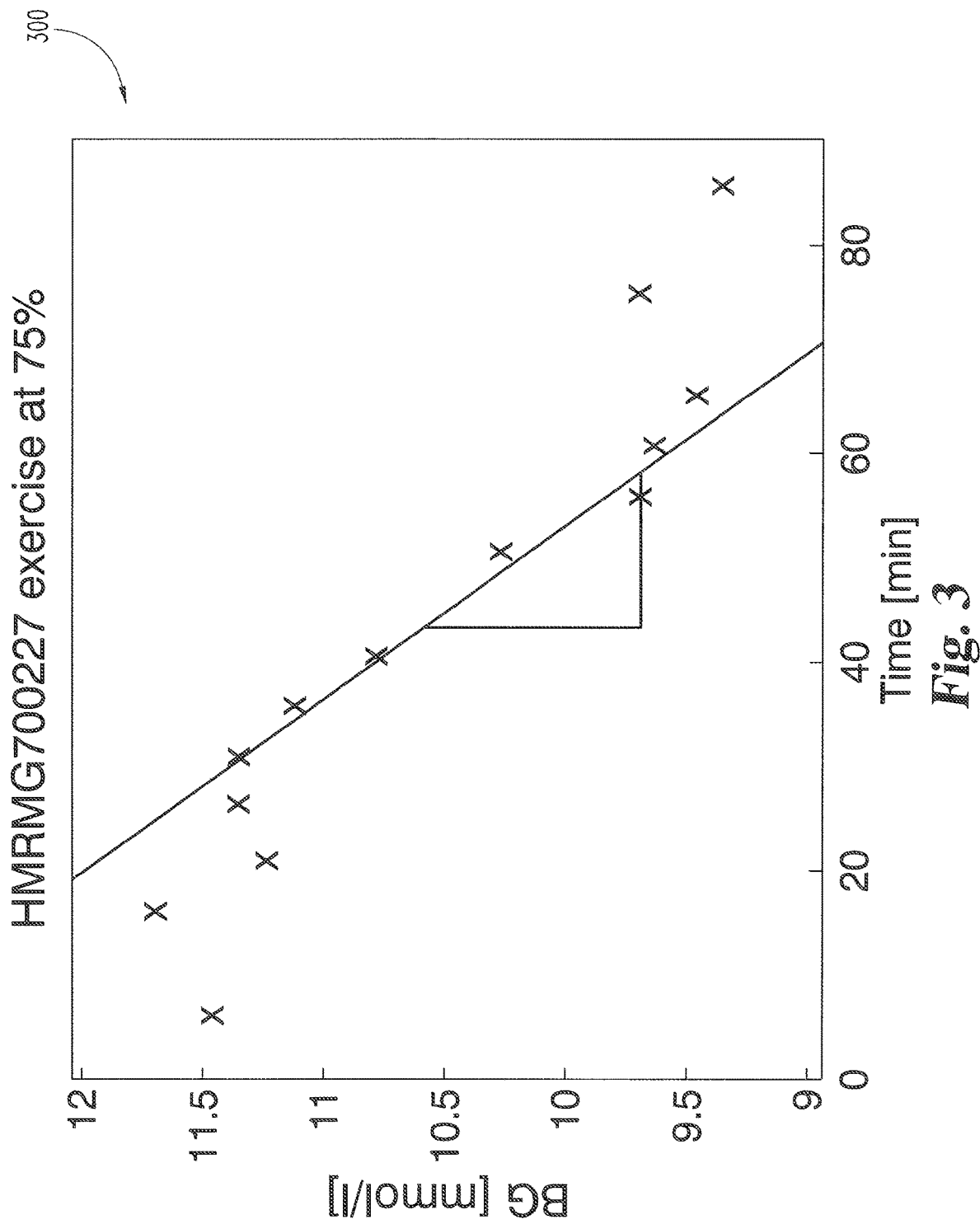
FIG. 3 shows a graph 300 that shows a linear regression slope of the drop in glucose concentration resulting from exercise.

The resulting data was used to find out what parameters the drop in blood glucose concentration depends. Several hypotheses were tested, first empirically; then statistically. FIG. 2 shows one example of a graph 200 that illustrates a drop in blood glucose concentration as a result of exercise at the intensity of 75% of the maximum heart rate for an individual patient. As can be seen in FIG. 2, the drop in blood glucose concentration starts and ends with a small delay, and the drop appears to be linear during the exercise. FIG. 3 shows a graph 300 that illustrates the linear nature of the drop in glucose concentration resulting from exercise, and more particularly, it shows the slope of the linear drop. Using linear regression, a straight line was fitted through the glucose measurement points. As mentioned before, there was a delay between when the exercise started and when the glucose concentration started to drop. Due to this warm up or delay phase, the slope for the glucose concentration drop in this example was calculated based on glucose measurements collected 10 minutes after the exercise started. The slope was also calculated based on a 40 minute period, because the effect of the exercise tends to last longer than the exercise itself.

Figure 4:
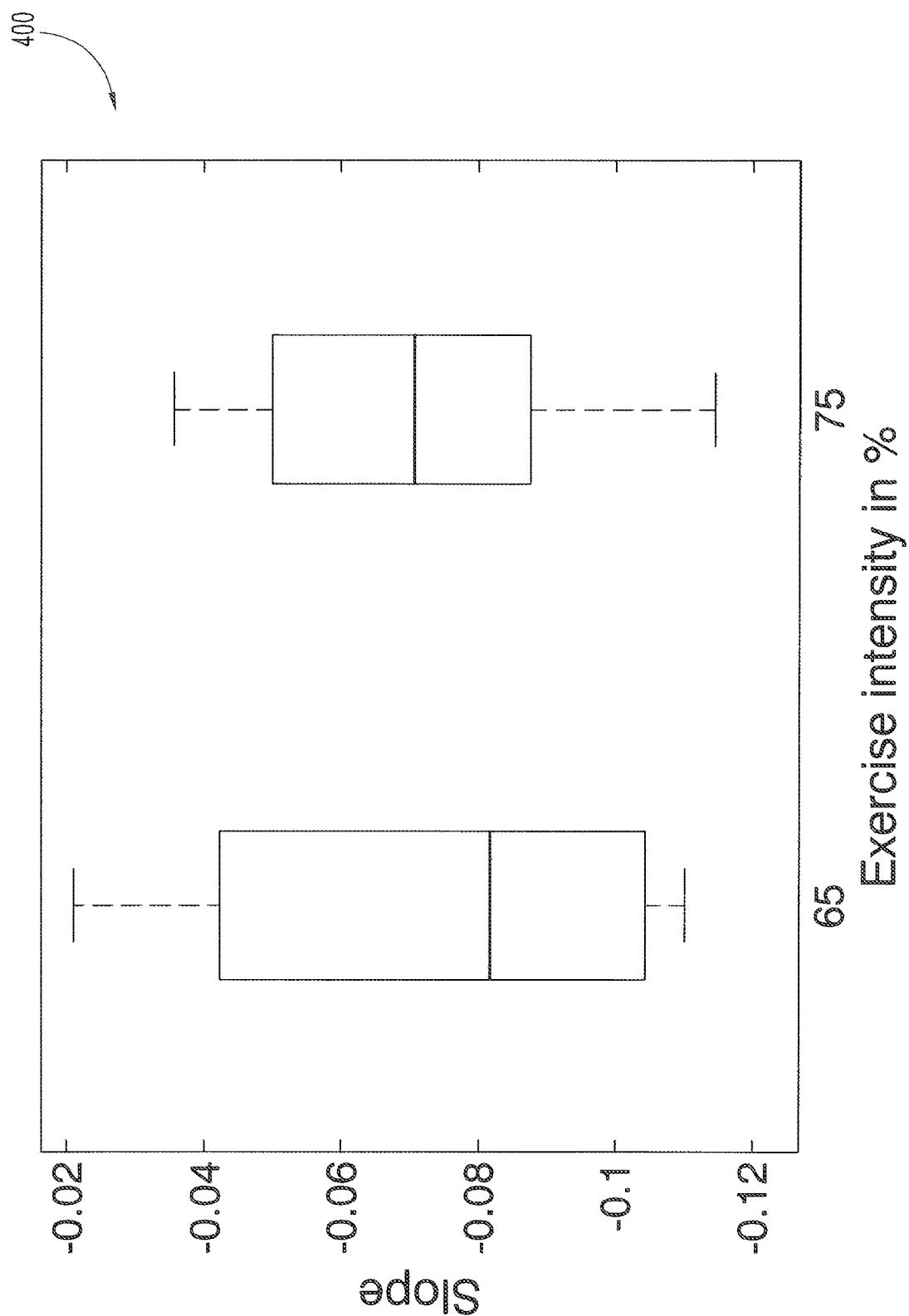
FIG. 4 shows a box-plot graph comparing the slopes at 65% and 75% exercise intensities, according to at least one embodiment of the present disclosure.

Several factors were tested to determine if they affected the slope of the linear glucose drop due to aerobic exercise. For example, as mentioned before, it was previously thought that the drop in blood glucose concentration depended on the intensity of physical activity. However, it was unexpectedly discovered that the intensity of aerobic physical activity did not affect the slope of the drop in glucose concentration resulting from physical activity. For instance, FIG. 4 shows a box-plot graph 400 comparing the slope means at 65% and 75% intensity. As can be seen, the box-plot graph 400 shows that the slope means are nearly identical for both intensities. This in turn suggests that at least for this range of exercise intensity, the drop in blood glucose concentration is independent of the exercise intensity. A normality test was passed that indicated this data can be considered as normally distributed. In addition, statistical tests showed that the slope means at the two exercise intensities were statistically the same or indistinguishable.

Figure 5:
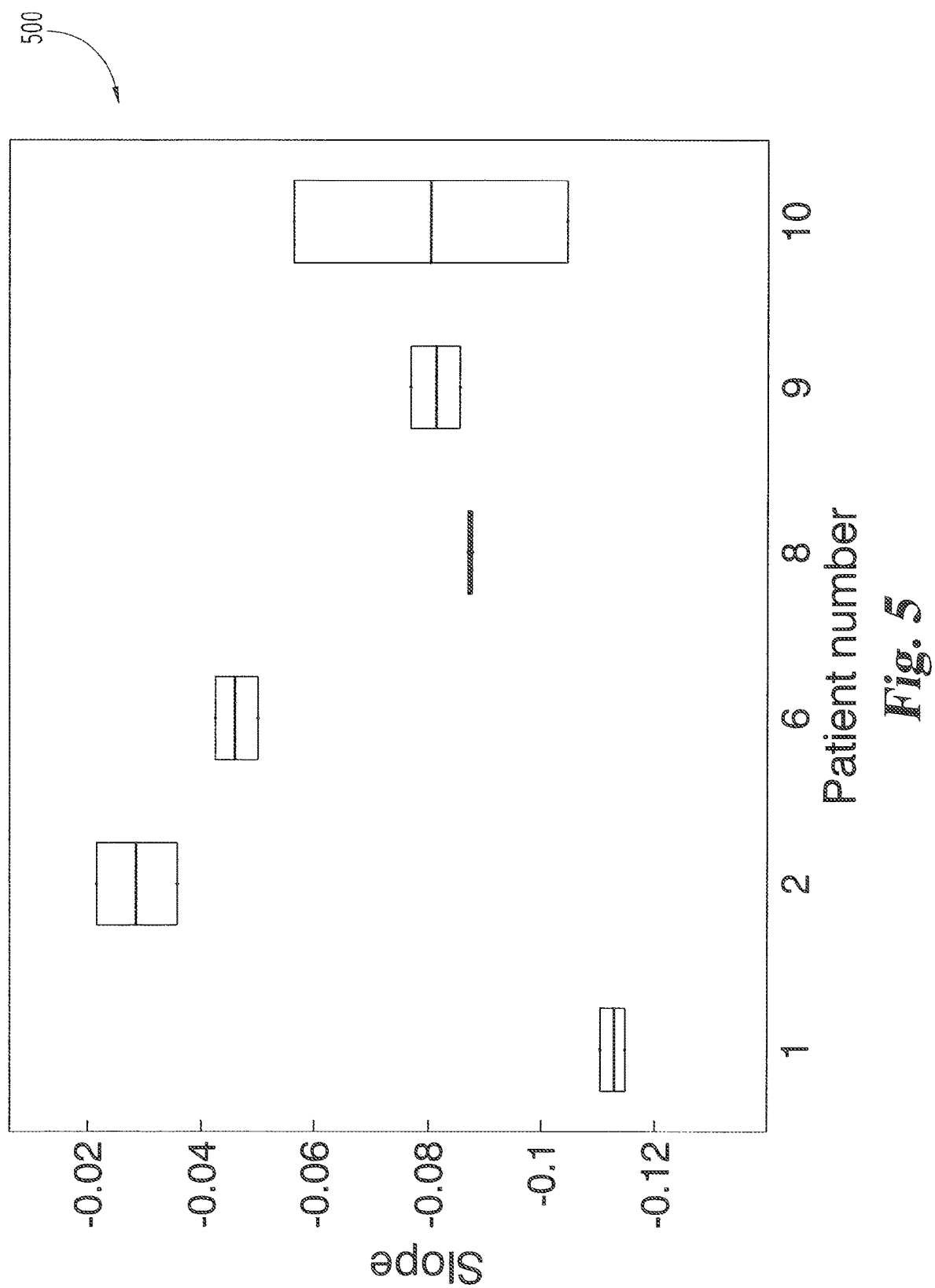
FIG. 5 shows a box-plot graph comparing the slopes between different patients.

Patient variability was another factor analyzed to see if affected the slope of the glucose concentration decrease. It was found that the slope strongly depends on the individual patient. Previous studies have shown that the behavior concerning meals is different for every patient. This leads to the assumption that the behavior concerning physical activity is different for every patient as well. Considering, that the intensity of the exercise has no influence, it was assumed to have two equivalent measurements for each patient. Box-plot graph 500 in FIG. 5 shows that variability of the various slopes between patients, which confirms the hypothesis. An analysis of variance (ANOVA) test shows that slopes are statistically significantly different for every patient with a p-value of 0.0115 (a value below 0.05 is considered significant). This dependence on the patient implies that the model parameters need to be estimated for every individual.

Several other factors were tested for their influence on the slope, but none of them gave any statistically conclusive results. The factors considered include gender, age, body mass index (BMI), insulin level and blood glucose level. To keep the model simple, only the significant influences were retained, which were patient variability and the presence of exercise.

The embodiment of the exercise model was designed based on these observations. From these observations, it was determined that the number of parameters needed to predict the effects of exercise on blood glucose levels were dramatically reduced. This simplicity in the model allows the effects of exercise to be accounted for in real world situations. Once the individual's parameters are determined (i.e., the slope in the drop of glucose concentration resulting from exercise and the delay of the exercise effect), the individual merely has to make a binary, exercise input ($U_{ex}$) of either 0 or 1, depending on whether the patient is at rest or exercising in order to account for the effect of rest or exercise. This elegant model is a direct consequence of the above-discussed finding that the blood glucose drop within certain activity levels is independent of the exercise intensity.

Again as was alluded to above in the discussion of FIG. 1 and Equation 6, the effect of this exercise input is modeled as an increase in glucose effectiveness at zero insulin or insulin independent glucose uptake 110 ($S_{g,zero}$), depending on the insulin-glucose model used. Again, the exercise glucose effectiveness 112 ($S_{g,ex}$) is another source for reducing the blood glucose amount 102 (Q), and like the glucose effectiveness at zero insulin 110 ($S_{g,zero}$) parameters in Equation 3, the exercise glucose effectiveness 112 ($S_{g,ex}$) parameter is proportional to blood glucose amount 102 (Q). As noted before, Equation 3 was modified to incorporate the exercise glucose effectiveness 112 ($S_{g,ex}$) factor by modeling as an exercise-induced increase in glucose effectiveness at zero insulin 110 ($S_{g,zero}$). The exercise glucose effectiveness 112 ($S_{g,ex}$) factor should be zero when no effect of exercise is present and take a positive value in the opposite case. The exercise input ($U_{ex}$) takes this into account. In addition, the effect of exercise in reducing blood glucose concentrations (Q) is not instantaneous and therefore a time constant for exercise glucose effectiveness 112 ($S_{g,ex}$) parameter is accounted for in this model as well. Consequently, the change in exercise glucose effectiveness 112 ($S_{g,ex}$) and delay can be accounted for in the following equation:

$$\frac{dS_{g,ex}}{dt} = -a_{ex}S_{g,ex} + K_{ex}a_{ex}U_{ex} \qquad \text{Equation 7}$$

where:
$S_{g,ex}$=Exercise glucose effectiveness [min$^{-1}$]
$a_{ex}$=Inverse of time constant for exercise effect [min$^{-1}$]
$K_{ex}$=Exercise sensitivity [min$^{-1}$]
$U_{ex}$=Exercise input [-]

Exercise sensitivity ($K_{ex}$) defines the amplitude of the drop in blood glucose levels during exercise for an individual, and the inverse time constant for exercise effect ($a_{ex}$) defines how quickly the exercise effect appears and disappears in the individual. Simple blood glucose readings during a clinical or home based exercise test can be used to determine these parameters for an individual. Once these parameters are determined, all that is required to model the effect of exercise is the single binary, exercise input ($U_{ex}$). Again, the exercise input ($U_{ex}$) has a value of zero (0) when no exercise is being performed and a value of one (1) during periods of exercise. This resulting model is independent of aerobic exercise intensity and does not require the complexity of collecting additional information during exercise, such as heart rate, blood pressure or venous oxygen levels. By not depending on these measures of exercise intensity, no additional measurement devices are required, which in turn results in lower costs and more patient comfort. In this sense the exercise input is the only non-constant and measured parameter for the model to consider the aerobic exercise on blood glucose levels for an individual. The exercise input can be monitored with an exercise monitoring device. For example the exercise monitoring device can be realized in that the patient can simply set the exercise input ($U_{ex}$) by, for example, pressing a button or other input on a glucose meter or other device. However, the exercise monitoring device can also be realized so that this exercise input ($U_{ex}$) can also be automatically set through a medical device capable of detecting changes in physical activity, such as through pedometers, heart rate monitors, etc. With the heart rate monitor example, if the heart rate is lower than a given limit, the patient is at rest, and the exercise input ($U_{ex}$) is set to zero (0). On the other hand when the heart rate is higher, the patient is considered physically active, and the exercise input ($U_{ex}$) is set to one (1).

Figure 6:
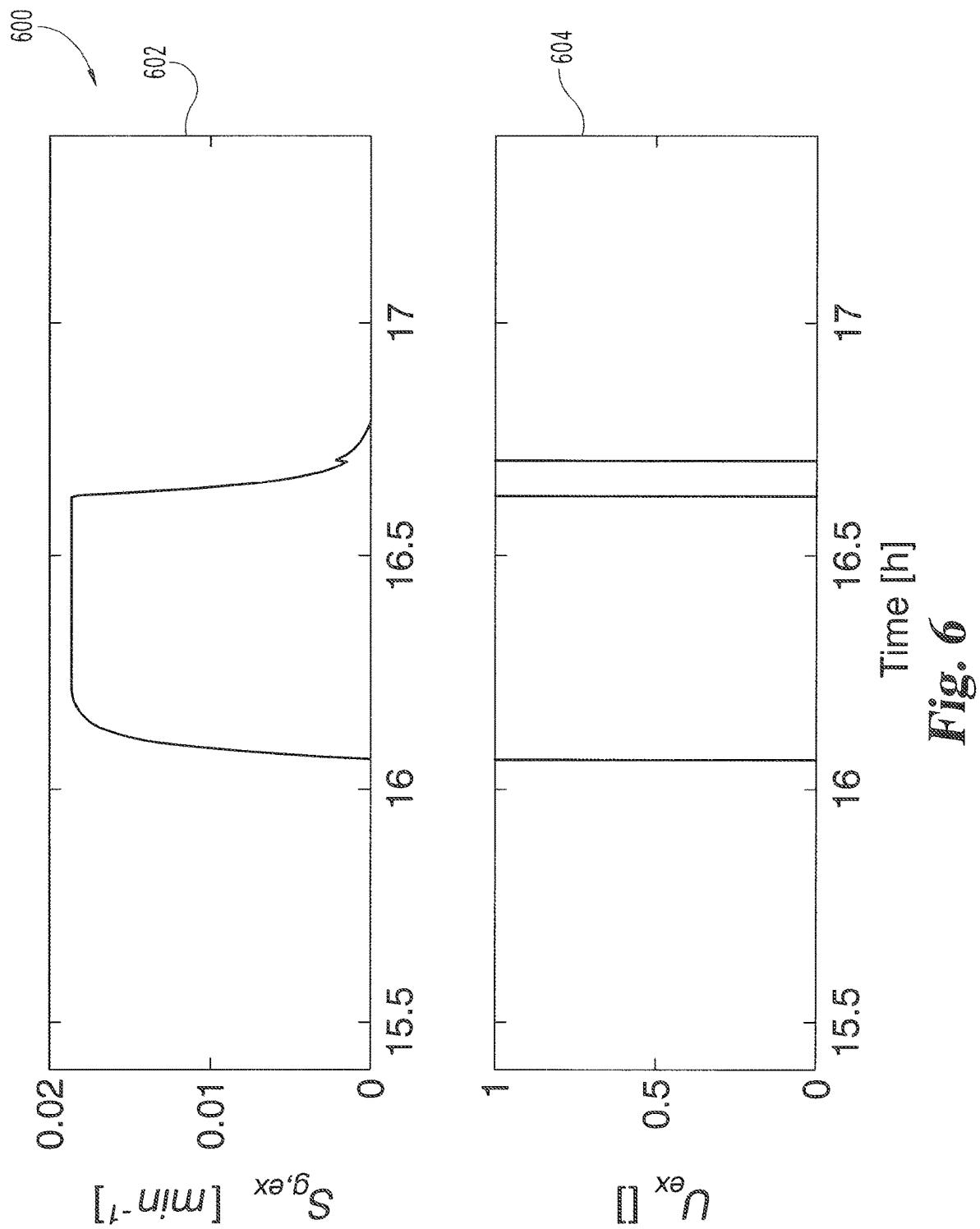
FIG. 6 shows a graph with an upper section that shows the exercise glucose effectiveness value ($S_{g,ex}$) and a lower section that shows the corresponding exercise input ($U_{ex}$), according to at least one embodiment of the present disclosure.

FIG. 6 shows a graph 600 that provides an example of the behavior for this exercise model. In this illustrated example, the exercise intensity for the patient was 65% of their maximum heart rate. As can be seen, the upper section 602 of the graph 600 shows the value of the exercise glucose effectiveness ($S_{g,ex}$) factor over time, and the lower section 604 shows the corresponding exercise input ($U_{ex}$).

Figure 7:
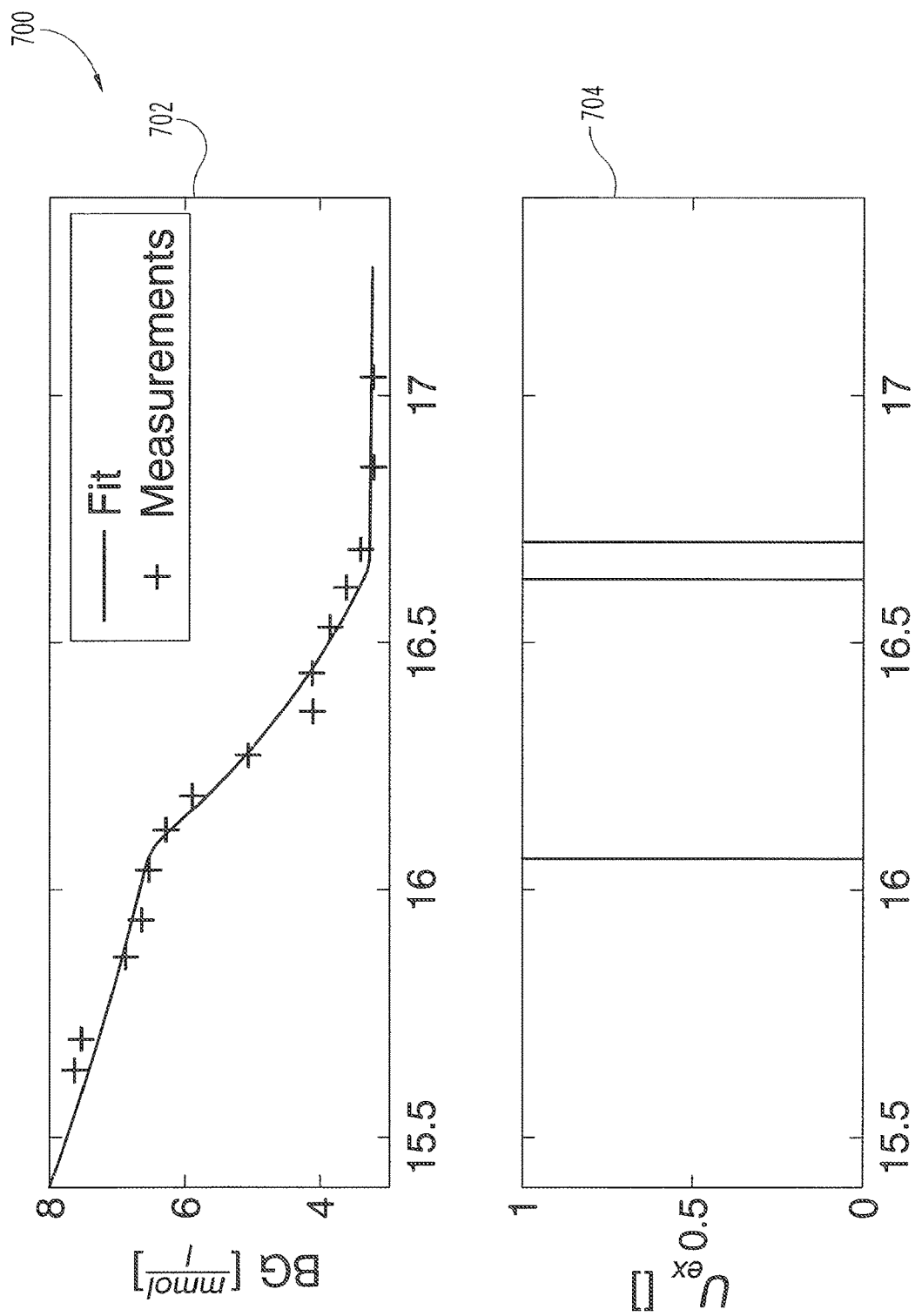
FIG. 7 shows a graph with an upper section that shows the glucose concentration measurements along with a fit line generated by an exemplary embodiment of the exercise model and a lower section showing the corresponding exercise input ($U_{ex}$).

This exercise model was tested by identifying the model parameter using clinical data. The exercise model showed good fitting capabilities for almost all patients. Graph 700 in FIG. 7 shows an example of how the exercise model fits to actual blood glucose readings. In this example, the exercise intensity for the patient was 65% of their maximum heart rate. The graph 700 has an upper section 702 that shows the glucose concentration measurements along with a fit line generated by the exercise model, and a lower section 704 shows the corresponding exercise input ($U_{ex}$). As can be seen, after the exercise begins, which is signified by the exercise input ($U_{ex}$) being equal to one in the lower section 704 of the graph 700, the fit line slopes in a generally linear fashion in the upper section 702, thereby corresponding to the drop in blood glucose concentration due to exercise. It should be appreciated from the graph 700 that the model shows good capabilities in modeling blood glucose concentration reductions due to exercise.

This model can be used in all products and methods that rely on a dynamical model of the blood glucose concentration. As it completes existing models, its range of use is extended. For example, this exercise model can be used in an automated pancreas (AP). In fact most of the recent closed-loop algorithms for automated pancreases rely on model predictions. Completing these predictions is essential if such an algorithm is to be commercially implemented. The exercise model described herein helps to provide this complete algorithm. In another example, the model can for insulin injection optimization. Optimizing the insulin injection profile for insulin pumps allows the patient to have better glycemic control. This model can also be used in model-based bolus calculators. While giving bolus recommendations, a planned exercise session could be considered, thus reducing the risk of hypoglycemia. It can also be used for educational tools. Showing patients what the effect of exercise on their blood glucose levels is, might be a motivation to exercise more while being aware of the underlying risks and thus the quality of life may be increased. It is further envisioned that this model can be used in conjunction with an exercise indicator to give the patient advice on care that he or she has to take (i.e., eat carbohydrates, adjust his insulin medication) before starting an aerobic exercise. It should be recognized that this model can be used in other situations as well.

Figure 8:
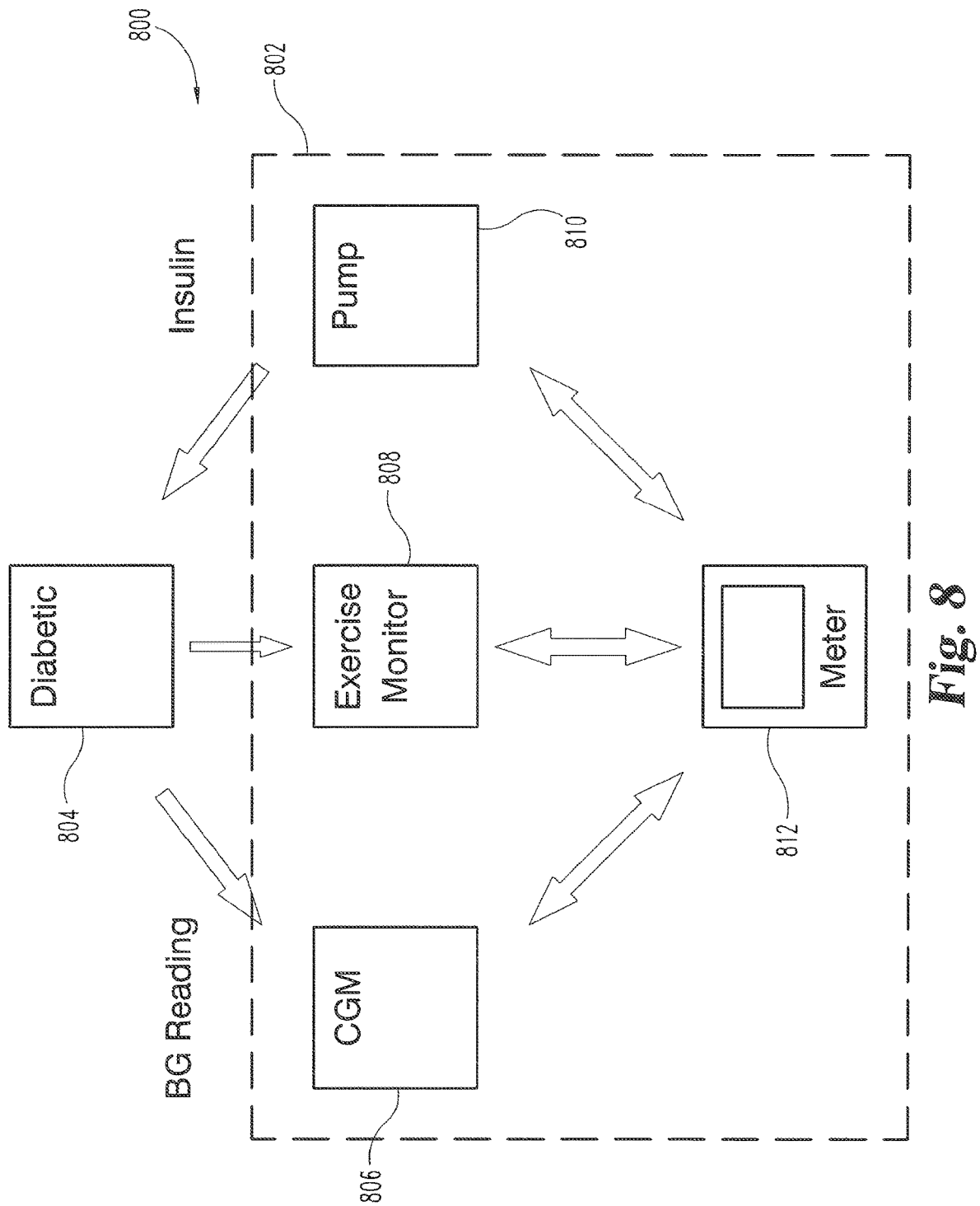
FIG. 8 shows a block diagram of a blood glucose monitoring system that utilizes the exercise model, according to at least one embodiment of the present disclosure.

An embodiment of this model being used in an automated pancreas system will now be described initially with reference to FIG. 8. FIG. 8 includes a block diagram of a blood glucose monitoring system 800 that utilizes the above described exercise model. In this system 800, an automated pancreas system 802 monitors and controls blood glucose levels of a diabetic patient 804. The automated pancreas system 802 includes a continuous glucose monitor (CGM) 806, an exercise monitor 808, an insulin pump 810, and a glucose meter 812. The continuous glucose monitor 806 continuously monitors blood glucose readings from the patient 804, and the continuous glucose monitor 806 transmits the blood glucose readings to the meter 812 for analysis. While the illustrated automated pancreas system 802 uses a continuous glucose monitor, it should be recognized that discrete type (e.g., finger stick type) glucose monitors can be used as well as other types of glucose monitors. An exercise monitor 808 is used to determine whether or not the patient 804 is performing aerobic exercise. The exercise monitor 808 can for example include a heart rate monitor that monitors the patient's heart rate to detect aerobic activity once the heart rate exceeds a threshold level. Of course, other devices can be used to detect aerobic activity. For this exercise model, the exercise monitor 808 only needs to transmit a binary signal indicating whether the patient is performing an aerobic activity or not (i.e., 0 or 1 for the exercise input $U_{ex}$). However, for other purposes, the exercise monitor 808 can transmit additional physiological data to the meter 812. For instance, the exercise monitor 808 can transmit a cardiogram of the patient 804 so that a physician can monitor the overall health of the patient 804. In another example, the exercise monitor 808 transmits the raw exercise data to the meter 812, and the meter 812 determines whether the patient 804 is performing aerobic exercise. In other variations, the exercise monitor 808 can be eliminated such that the diabetic patient 804 (or someone else) manually indicates whether or not exercise is being performed via the meter 812. Based on instructions from the meter 812, the insulin pump 810 delivers the appropriate insulin amount to the patient.

In the FIG. 8 system 800, the meter 812 processes an algorithm that incorporates the exercise model in conjunction with other glucose control models, such as the previously described ABP model, so as to control the insulin delivery to the patient 804 via the insulin pump 810. The meter 812 includes components commonly found in glucose meters and other types of monitoring devices, like one or more processors, memory, displays, speakers, input devices, and output devices. The processor of the meter 812 using the above discussed model is able to predict future blood glucose levels, and if needed, take corrective actions such as increasing insulin dosages and/or alerting the patient 804 when potential problematic blood glucose levels are predicted to occur (e.g., hypoglycemia). The meter 812 in other examples can be replaced by other computing devices, such as a personal computer, medical device, and/or smart phone, to name just a few. In the illustrated embodiment, the various components of the automated pancreas system are illustrated as separate components, but it should be recognized that one or more of these components can be integrated together to form a single unit.

Figure 9:
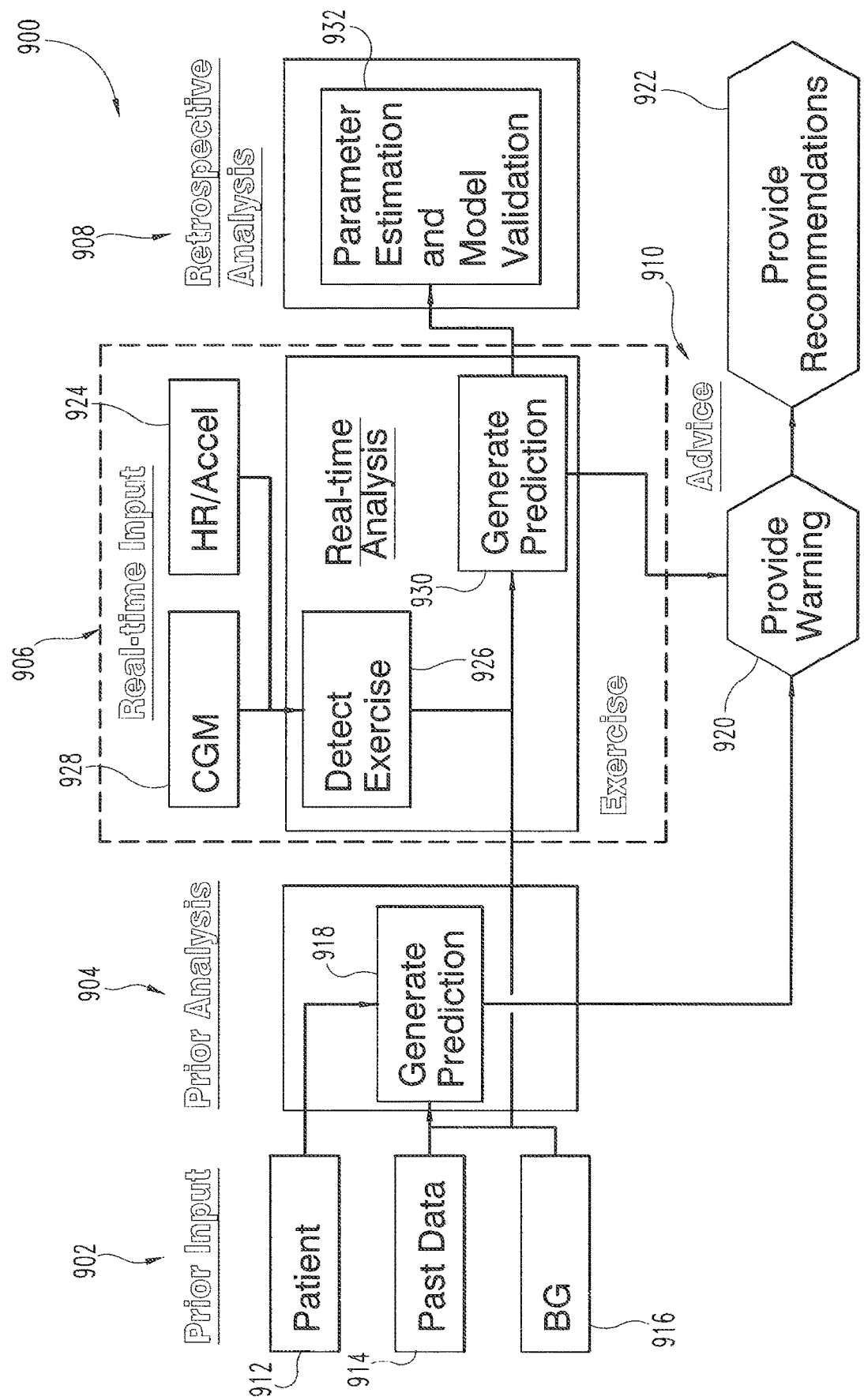
FIG. 9 shows a flow diagram of a technique for monitoring blood glucose levels in a patient during exercise utilizing the exercise model, according to at least one embodiment of the present disclosure.

FIG. 9 shows a flow diagram 900 of a technique for monitoring blood glucose levels in a patient during exercise utilizing the above discussed exercise model. For explanation purposes the technique in the flow diagram 900 will be described with reference to the monitoring system 800 shown in FIG. 8, but it should be recognized that it can be utilized with other systems. As can be seen, the flow diagram 900 includes several sections, including a prior to exercise input section 902, a prior to exercise analysis section 904, an exercise section 906, a retrospective analysis section 908, and an advice section 910.

In the prior to exercise input section 902, patient data 912, past or historical data 914, and current blood glucose data 916 are entered into the meter 812. Patient data for example can include vital statistics, carbohydrates consumed, etc. Past data can includes factors for calculating the exercise glucose effectiveness 112 ($S_{g,ex}$). To utilize the exercise model, the exercise sensitivity ($K_{ex}$) and inverse time constant ($a_{ex}$) of Equation 7 are determined for the individual patient 804 so that the exercise glucose effectiveness 112 ($S_{g,ex}$) factor (Equation 6) can be modeled. These factors can be determined by performing an aerobic exercise test in which blood glucose values are periodically read, such as via the continuous glucose monitor 806, in the manner as described before for the clinical studies. These factors are then determined by the meter 812 or a computer via linear regression or other techniques. While these initial parameters can be determined in a doctor's office, considering only blood glucose data is required, these initial set-up tests can performed at home or elsewhere. In this case, the meter 812 can include a script that guides the patient 804 through the initial testing process for in initializing the exercise model. For example, the meter 812 can instruct the patient to ingest (or not) a specific carbohydrate amount before exercise, and then run on their treadmill for 30 minutes so that the patient's heart rate is within the aerobic exercise heart rate range. During the exercise, the meter 812 can monitor the glucose levels via the continuous glucose monitor 806 (or other type of glucose monitor) and the patient's vital statistics via the exercise monitor 808 to ensure the test is being properly performed.

After the set-up test is performed, the meter 812 determines the exercise effectiveness ($S_{g,ex}$) factors in the manner as described above with reference to FIGS. 3 to 7. The resulting exercise model can be incorporated into other models, like the ABP model discussed above, that incorporate other factors such as carbohydrate consumption and insulin dosage. Equation 6 is just one example of this combined model approach, but it is envisioned that the exercise model can be incorporated into other models. Before the aerobic exercise or other physical activity, the meter 812 in stage 918 (prior to exercise analysis section 904) generates a prediction based on the calculated model along with other data collection in section 902, like the blood glucose data 916. If a potentially dangerous condition is predicted, like hypoglycemia, the meter 812 provides a warning in stage 920, such as by displaying a message warning the user of the potential dangerous condition via an interface device. In addition, if needed, the meter 812 in stage 922 provides recommendations for taking corrective action, such as recommending a particular meal so as to avoid hypoglycemia. In another example, the infusion profile of the insulin pump 810 is adjusted so as to avoid any problematic glucose levels. The interface device can be a display, a diode or diode array, a loudspeaker or another device capable of transport a message to a person involved.

In a further embodiment not shown in the figures the input section 902 comprises in addition or alternatively to the detect exercise stage 926 an exercise input. To perform this exercise input the system comprises an input device which is connected to the exercise monitor 808, so that the patient can itself program the automated pancreas system 802 i.e. the system for an intended exercise. Hence the automated pancreas system 802 can adjust the insulin delivery based on the predicted blood glucose levels on account on an intended exercise. The input device can be a button, a touch sensitive display or any other device capable to process a input form a person involved.

In the exercise section 906, the exercise monitor 808 in stage 924 monitors the patient's activity, such as their heart rate and/or acceleration, so that the meter 812 is able to automatically detect initiation of the exercise in stage 926. Again, it should be appreciated that the user can manually signify the start of an exercise by pressing a button on the meter 812 and/or interfacing with the meter 812 in some other way. The continuous glucose monitor 806 provides glucose measurements to the meter in stage 928, and based on those measurements as well as other data, predicts future blood glucose levels in stage 930 using the above described exercise model in a manner similar to the one previously described with reference to stage 918. If the meter 812 predicts a potential problem, such as hypoglycemia, the meter provides a warning in stage 920 along with a recommended corrective course of action in stage 922. For instance, the insulin infusion profile of the insulin pump 810 can be adjusted. After the exercise, the meter 812 can perform retrospective analysis in stage 932 so as to validate the model and re-estimate the parameters.

Figure 10:
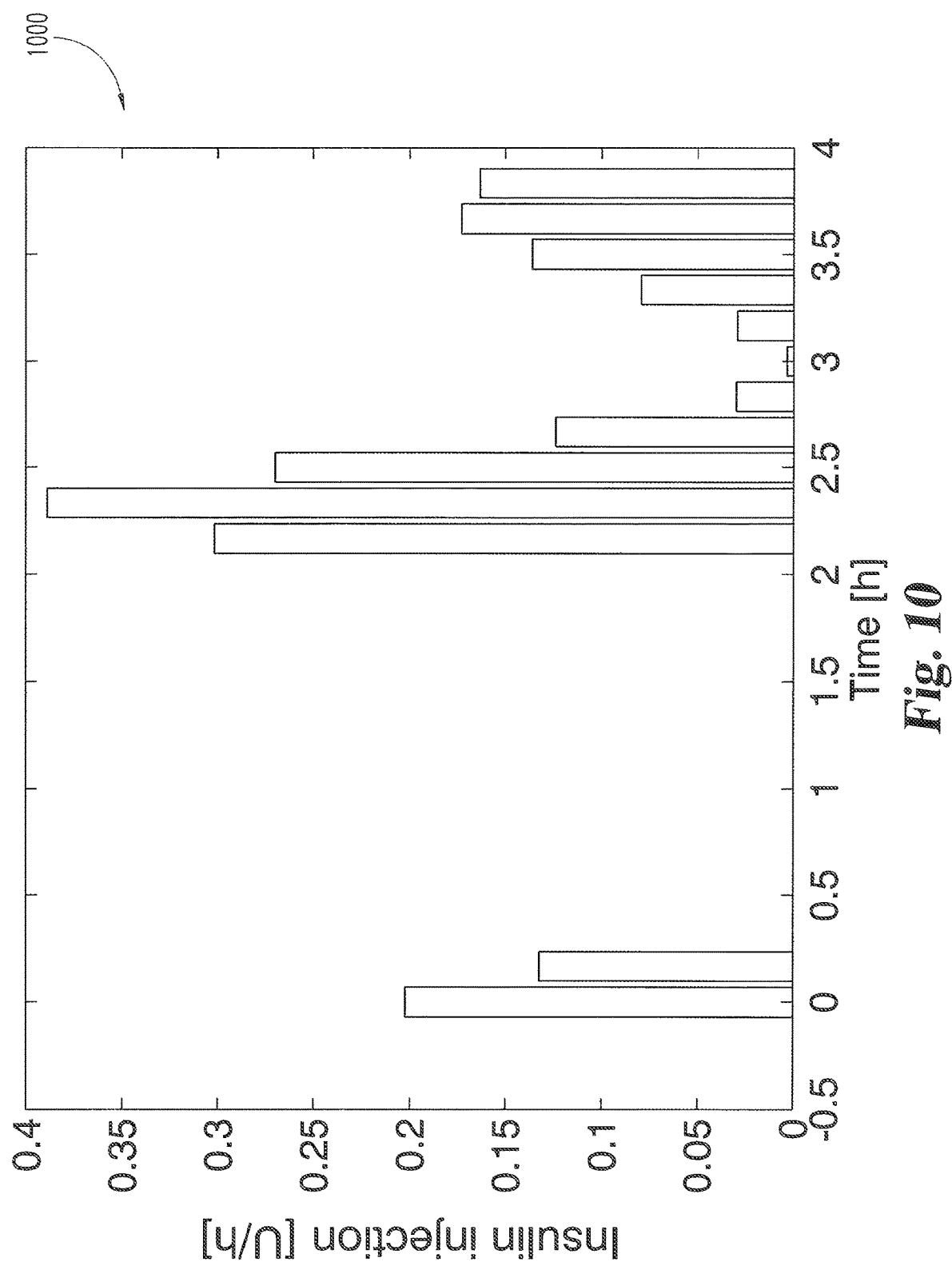
FIG. 10 shows an example of an optimized insulin infusion profile, according to at least one embodiment of the present disclosure.
Figure 11:
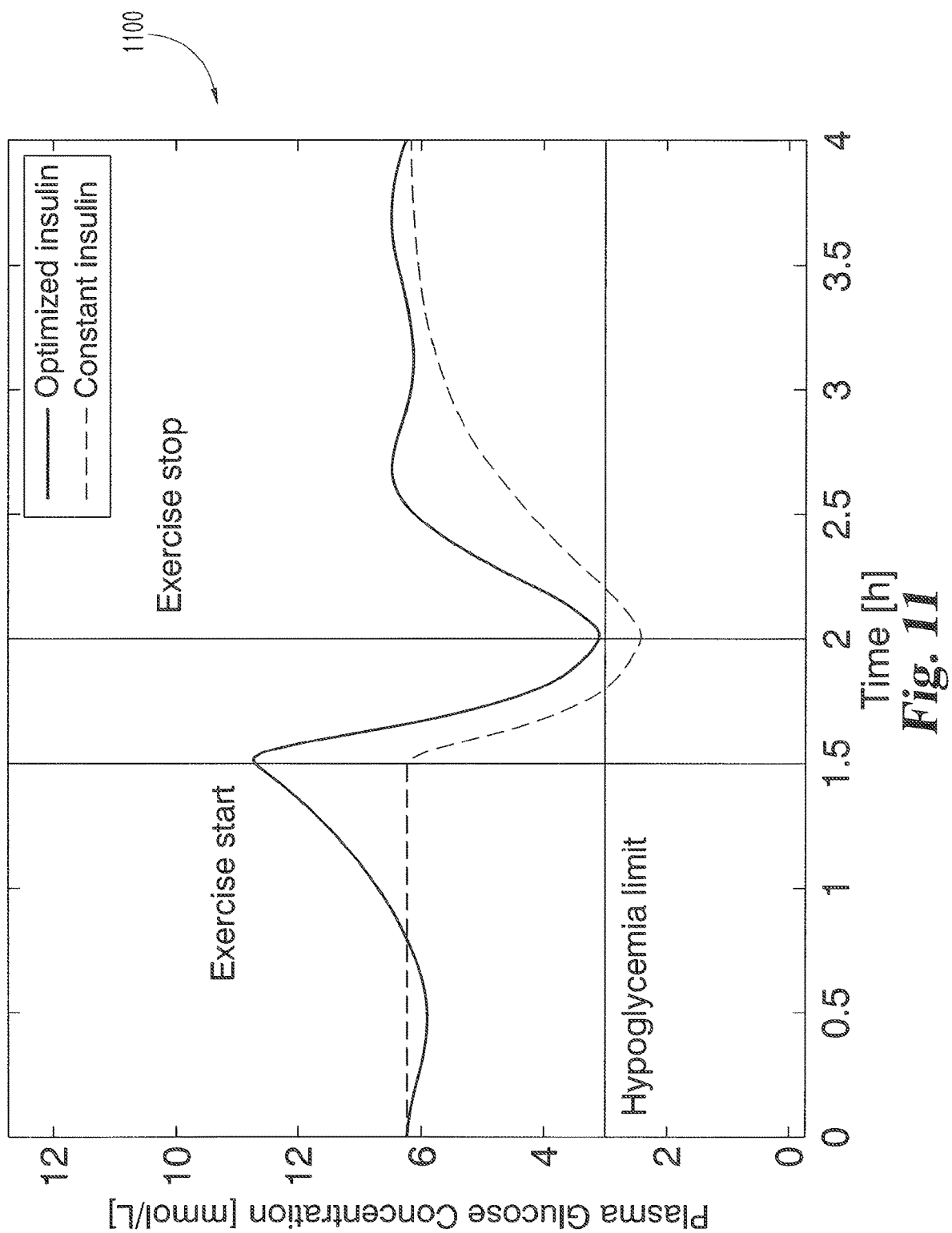
FIG. 11 shows a simulation of a blood glucose profile obtained with the optimized insulin infusion profile of FIG. 10.

As mentioned before, the exercise model can help to optimize insulin injection or infusion profiles. Optimizing the insulin injection profile for insulin pumps as well as in other situations allows patients to have better blood glucose control. FIG. 10 shows an example of an insulin infusion profile 1000 that was optimized based at least in part on the above-discussed exercise model. FIG. 11 shows a simulation 1100 of the blood glucose profile obtained with the optimized insulin profile of FIG. 10 as compared to a constant insulin profile. As shown, the blood glucose concentration drops with both profiles during exercise. However, the optimized insulin profile of FIG. 7 avoids a hypoglycemic event, whereas the constant insulin infusion profile drops below the hypoglycemic limit.

It should be appreciated that the term "exercise" as used herein is meant to encompass a broad range of physical activities, and it is not limited to exercises performed in a gym or clinical setting. Not only does the exercise include traditional exercises, such as running, swimming, walking, biking, rowing, calisthenics, and the like, but it also can include other forms of physical activities that raise the heart rate, such as climbing, digging, gardening, building, and/or work activities, to name just a few examples.

While various embodiments of systems and methods for considering the effect of aerobic exercise on blood glucose levels for an individual have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

The invention claimed is:

1. A system for considering the effect of aerobic exercise on blood glucose levels for an individual to deliver insulin based on an optimized insulin injection profile to reduce a risk of a hypoglycemic episode at least partially due to aerobic exercise, comprising:
    a computing device comprising a device processor and a device memory storing device programming instructions that, when executed by the device processor, cause the device processor to implement the device programming instructions for generating a prediction of future blood glucose levels for the individual at least partly based on an exercise model, wherein the exercise model excludes an aerobic exercise intensity parameter to reduce a complexity of parameters processed by the computing device to generate the prediction while including at least one exercise parameter to reduce the risk of the hypoglycemic episode; and
    an automated pancreas communicatively coupled to the computing device, the automated pancreas comprising a pancreas processor and a pancreas memory storing programming instructions that, when executed by the pancreas processor, cause the pancreas processor to implement the programming instructions for collecting one or more blood glucose readings of the individual as a parameter of the exercise model and taking an action at least based on the prediction from the exercise model, wherein the action comprises optimizing an insulin injection profile to prevent the hypoglycemic episode and adjusting a delivery of insulin to the individual based on the optimized insulin injection profile, wherein the optimized insulin injection profile is varying over a period of time and is based on the prediction, and wherein the exercise model is based on one of the following equations:

where
Sg,ex=Exercise glucose effectiveness;
aex=Inverse of time constant for exercise effect;
Kex=Exercise sensitivity; and
Uex=Exercise input; or
where:
Q=glucose amount in the accessible compartment;
X=insulin action;
Sg,zero=Glucose effectiveness at zero insulin;
Sg,ex=Exercise glucose effectiveness;
Uendo=Insulin independent endogenous production;
Ug,gut=carbohydrate intake rate; and
g→mmol is a constant conversion factor that transforms grams of carbohydrates to mmol.

2. The system according to claim 1, further comprising an exercise monitoring device in communication with the computing device, wherein the exercise monitoring device is capable of detecting the occurrence of an exercise and sending an input signal to the computing device for whether the aerobic exercise is being or will be performed by the individual or not.

3. The system according to claim 1, further comprising an interface device in communication with the computing device, wherein the interface device is operable to alert the individual of a dangerous blood glucose level condition via the interface device.

4. A method of considering the effect of aerobic exercise on blood glucose levels for an individual to deliver insulin based on an optimized insulin injection profile to reduce a risk of a hypoglycemic episode at least partially due to aerobic exercise, comprising:
    generating with a computing device a prediction of future blood glucose levels for the individual at least partly based on an exercise model, wherein the exercise model excludes an aerobic exercise intensity parameter to reduce a complexity of parameters processed by the computing device to generate the prediction while including at least one exercise parameter to reduce the risk of the hypoglycemic episode; and
    taking an action with the computing device at least based on the prediction from the exercise model, wherein said taking the action with the computing device includes utilizing an automated pancreas for collecting one or more blood glucose readings of the individual as a parameter of the exercise model and optimizing an insulin injection profile to prevent the hypoglycemic episode, performing a corresponding bolus calculation, and adjusting a bolus delivery to the individual that is based on the optimized insulin injection profile, wherein the optimized insulin injection profile is varying over a period of time and is based on the prediction, and wherein the exercise model is based on one of the following equations:

where
Sg,ex=Exercise glucose effectiveness;
aex=Inverse of time constant for exercise effect;
Kex=Exercise sensitivity; and
Uex=Exercise input; or
where:
Q=glucose amount in the accessible compartment;
X=insulin action;
Sg,zero=Glucose effectiveness at zero insulin;
Sg,ex=Exercise glucose effectiveness;
Uendo=Insulin independent endogenous production;
Ug,gut=carbohydrate intake rate; and
g→mmol is a constant conversion factor that transforms grams of carbohydrates to mmol.

5. The method according to claim 4, wherein the parameters include a non-constant and measured parameter, the non-constant and measured parameter is an Exercise Input indicating whether an exercise is performed or not.

6. The method according to claim 4, wherein the exercise model incorporates an exercise sensitivity value that represents change in the blood glucose level over time during exercise without considering intensity of the exercise.

7. The method according to claim 4, wherein the exercise model accounts for a change in the blood glucose level based on an amplitude of the change in the blood glucose level during exercise for the individual and how quickly the exercise effect appears and disappears in the individual along with an exercise input that considers whether or not an exercise is being performed without considering the intensity of the exercise.

8. The method according to claim 4, further comprising: receiving an exercise input with the computing device that the aerobic exercise is being performed by the individual.

9. The method according to claim 8, wherein the exercise input is a binary type input that signifies whether or not the aerobic exercise is occurring.

10. The method according to claim 8, wherein said receiving the exercise input includes receiving a manual input from the individual.

11. The method according to claim 8, wherein said receiving the exercise input includes receiving an automatic input from an exercise monitoring device.

12. The method according to claim 4, wherein said taking the action with the computing device includes alerting the individual of a dangerous blood glucose level condition.

13. The method according to claim 4, wherein said taking the action with the computing device includes providing an output that educates the individual about the effect of aerobic exercise on blood glucose levels for the individual.

14. The method according to claim 4, wherein the aerobic exercise occurs in a range from 65% to 75% of a maximum heart rate for the individual.

15. The method according to claim 4, further comprising: conducting an exercise study to determine the parameters for the exercise model.

16. The method according to claim 15, wherein only blood glucose concentrations during the exercise study are used to determine the parameters for the exercise model.

17. The method according to claim 4, wherein the exercise has a duration of no more than 90 minutes.

18. The method according to claim 4, wherein the exercise has a duration of no more than 45 minutes.

19. The method according to claim 4, wherein the exercise has a duration of no more than 30 minutes.

20. The method according to claim 4, wherein the computing device includes a glucose meter.

* * * * *